(12) United States Patent
Nanaumi

(10) Patent No.: US 9,125,591 B2
(45) Date of Patent: Sep. 8, 2015

(54) ACOUSTIC-WAVE MEASURING APPARATUS AND METHOD

(75) Inventor: Ryuichi Nanaumi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 515 days.

(21) Appl. No.: 13/088,495

(22) Filed: Apr. 18, 2011

(65) Prior Publication Data

US 2011/0263963 A1    Oct. 27, 2011

(30) Foreign Application Priority Data

Apr. 26, 2010   (JP) .................................. 2010-101300

(51) Int. Cl.
| | | |
|---|---|---|
| A61B 8/00 | (2006.01) | |
| A61B 8/08 | (2006.01) | |
| A61B 5/00 | (2006.01) | |
| A61B 8/13 | (2006.01) | |
| G01N 21/17 | (2006.01) | |

(52) U.S. Cl.
CPC .............. *A61B 8/0825* (2013.01); *A61B 5/0073* (2013.01); *A61B 5/0091* (2013.01); *A61B 5/0095* (2013.01); *A61B 5/4312* (2013.01); *A61B 8/13* (2013.01); *A61B 8/406* (2013.01); *A61B 8/42* (2013.01); *A61B 8/4281* (2013.01); *G01N 21/1702* (2013.01)

(58) Field of Classification Search
USPC ........................................................ 600/437
See application file for complete search history.

(56) References Cited

U.S. PATENT DOCUMENTS

| | | | | |
|---|---|---|---|---|
| 4,504,727 A | * | 3/1985 | Melcher et al. ........... | 219/121.62 |
| 4,896,673 A | * | 1/1990 | Rose et al. ................... | 600/439 |
| 5,377,006 A | * | 12/1994 | Nakata ........................... | 356/486 |
| 5,479,259 A | * | 12/1995 | Nakata et al. .................. | 356/487 |
| 5,781,294 A | * | 7/1998 | Nakata et al. .................. | 356/487 |
| 5,871,445 A | * | 2/1999 | Bucholz ........................ | 600/407 |
| 5,891,034 A | * | 4/1999 | Bucholz ........................ | 600/426 |
| 5,967,982 A | * | 10/1999 | Barnett ......................... | 600/429 |
| 6,146,390 A | * | 11/2000 | Heilbrun et al. .............. | 606/130 |

(Continued)

FOREIGN PATENT DOCUMENTS

| | | |
|---|---|---|
| CN | 101385638 A | 3/2009 |
| EP | 2036488 A2 | 3/2009 |

(Continued)

OTHER PUBLICATIONS

Manohar et al, "The Twente Photoacoustic Mammoscope: system overview and performace", Phys. Med. Biol. 50 (2005) 2543-2557.*

(Continued)

*Primary Examiner* — Nicholas Evoy
(74) *Attorney, Agent, or Firm* — Canon USA Inc. IP Division

(57) ABSTRACT

An acoustic-wave measuring apparatus includes a holding unit configured to hold a subject and an irradiation unit configured to irradiate the subject with light. An acoustic-wave detecting unit detects acoustic waves generated in the subject due to irradiation with the light; an image pickup unit acquires an image of the subject; and a measurement position on the image acquired by the image pickup unit is designated. A coordinate transforming unit transforms the coordinates of the measurement position on the image to coordinates of a corresponding position on the holding unit; and a position control unit moves at least one of the irradiation unit and the acoustic-wave detecting unit to the corresponding position on the holding unit.

26 Claims, 8 Drawing Sheets

(56) References Cited

U.S. PATENT DOCUMENTS

| | | | |
|---|---|---|---|
| 6,165,181 A * | 12/2000 | Heilbrun et al. | 606/130 |
| 6,167,145 A * | 12/2000 | Foley et al. | 382/128 |
| 6,405,072 B1 * | 6/2002 | Cosman | 600/426 |
| 6,490,467 B1 * | 12/2002 | Bucholz et al. | 600/407 |
| 6,585,651 B2 * | 7/2003 | Nolte et al. | 600/449 |
| 6,662,036 B2 * | 12/2003 | Cosman | 600/411 |
| 6,675,040 B1 * | 1/2004 | Cosman | 600/427 |
| 6,678,545 B2 * | 1/2004 | Bucholz | 600/426 |
| 6,920,347 B2 * | 7/2005 | Simon et al. | 600/424 |
| 6,979,292 B2 * | 12/2005 | Kanayama et al. | 600/437 |
| 7,068,867 B2 * | 6/2006 | Adoram et al. | 385/12 |
| 7,072,704 B2 * | 7/2006 | Bucholz | 600/407 |
| 7,277,594 B2 * | 10/2007 | Hofstetter et al. | 382/275 |
| 7,438,685 B2 * | 10/2008 | Burdette et al. | 600/439 |
| 7,567,834 B2 * | 7/2009 | Clayton et al. | 600/424 |
| 7,576,334 B2 * | 8/2009 | Ashkenazi et al. | 250/459.1 |
| 8,880,141 B2 * | 11/2014 | Chen | 600/407 |
| 2005/0004458 A1 * | 1/2005 | Kanayama et al. | 600/437 |
| 2005/0187471 A1 * | 8/2005 | Kanayama et al. | 600/437 |
| 2008/0021317 A1 * | 1/2008 | Sumanaweera | 600/437 |
| 2008/0221647 A1 * | 9/2008 | Chamberland et al. | 607/88 |
| 2010/0058870 A1 * | 3/2010 | Kobayashi | 73/596 |
| 2010/0249570 A1 * | 9/2010 | Carson et al. | 600/407 |
| 2010/0285518 A1 * | 11/2010 | Viator et al. | 435/29 |
| 2011/0054292 A1 * | 3/2011 | Hirson et al. | 600/407 |
| 2011/0066023 A1 * | 3/2011 | Kanayama et al. | 600/407 |
| 2011/0190617 A1 * | 8/2011 | Chen | 600/407 |
| 2011/0224532 A1 * | 9/2011 | Tanabe | 600/407 |
| 2012/0167693 A1 * | 7/2012 | Asao | 73/655 |
| 2012/0209104 A1 * | 8/2012 | Suzuki | 600/407 |
| 2012/0302866 A1 * | 11/2012 | Fukutani et al. | 600/407 |
| 2013/0044563 A1 * | 2/2013 | Watanabe et al. | 367/7 |
| 2013/0102865 A1 * | 4/2013 | Mandelis et al. | 600/328 |
| 2013/0109952 A1 * | 5/2013 | Motoki | 600/407 |
| 2013/0116537 A1 * | 5/2013 | Sato | 600/407 |
| 2013/0116539 A1 * | 5/2013 | Nagao | 600/407 |
| 2013/0131487 A1 * | 5/2013 | Nagao | 600/407 |
| 2013/0237799 A1 * | 9/2013 | Motoki | 600/407 |
| 2013/0237800 A1 * | 9/2013 | Yamamoto | 600/407 |
| 2013/0267856 A1 * | 10/2013 | Watanabe et al. | 600/476 |
| 2013/0274585 A1 * | 10/2013 | Wanda | 600/407 |
| 2013/0338474 A9 * | 12/2013 | Carson et al. | 600/407 |
| 2014/0107462 A1 * | 4/2014 | Wanda | 600/407 |
| 2014/0303498 A1 * | 10/2014 | Watanabe et al. | 600/437 |
| 2014/0316236 A1 * | 10/2014 | Umezawa | 600/407 |
| 2014/0316240 A1 * | 10/2014 | Nagao | 600/407 |
| 2014/0350358 A1 * | 11/2014 | Oikawa et al. | 600/301 |

FOREIGN PATENT DOCUMENTS

| | | |
|---|---|---|
| JP | 2005-517488 A | 6/2005 |
| JP | 2008086400 A | 4/2008 |
| WO | 03083779 A2 | 10/2003 |

OTHER PUBLICATIONS

Manohar et al., "Region-of-Interest Breast Studies Using the Twente Photoacoustic Mammoscope (PAM)," Photons Plus Ultrasound: Imaging and Sensing, Proc. of SPIE vol. 6437, 2007, pp. 643702-1-643702-9.

Manohar et al.,"The Twente Photoacoustic Mammoscope: system overview and performance", Physics in Medicine and Biology, May 18, 2005, pp. 2543-2557.

* cited by examiner

ACOUSTIC-WAVE MEASURING APPARATUS AND METHOD

BACKGROUND OF THE INVENTION

1. Field of the Invention

The present invention relates to an acoustic-wave measuring apparatus and an acoustic-wave measuring method. In particular, it relates to an acoustic-wave measuring apparatus that receives acoustic waves generated from a subject irradiated with light, as well as a method for controlling the apparatus.

2. Description of the Related Art

Photoacoustic tomography (PAT) is technique for in-vivo imaging using near-infrared light. In imaging with PAT, a subject, such as a living organism, is irradiated with pulsed light generated from a light source, and the light propagated and spread in the subject is absorbed by a light absorbing substance to generate acoustic waves (typically, ultrasonic waves). The mechanism of the generation of acoustic waves is known as the photoacoustic-wave effect. Tumorous tissue reacts to near-infrared light differently than peripheral tissue, it absorbs light more than the peripheral tissue to expand instantly and generate acoustic waves corresponding to the region that has absorbed the near-infrared light. A photoacoustic imaging apparatus, which is an acoustic-wave measuring apparatus, is an apparatus that receives the acoustic waves with an acoustic-wave detecting element and analyzes the received signal to thereby calculate information, such as spatial initial sound pressure distribution, on acoustic waves generated in the subject and forms an image based on the calculated information. Because the distribution of the generated sound pressure is related to a light absorption coefficient, diagnosis of a subject using the distribution related to the light absorption coefficient is currently being actively studied.

The acoustic-wave measuring apparatus that obtains readings of a living organism using the photoacoustic-wave effect uses a high-output short-pulse (several tens of nanoseconds) light source having a near-infrared wavelength. The near-infrared wavelength band, in which light absorption of living organisms is low, is known as a biological window. Near-infrared light in the biological window can reach deep into living organisms without causing damage. Nevertheless, in an acoustic-wave measuring apparatus using PAT technology it is necessary to prevent the light from irradiating the observer, in particular, the eyes.

To that end, for example, an apparatus described by Manohar, et al., entitled "Region-of-interest breast studies using the Twente Photoacoustic Mammoscope (PAM)", Proc. of SPIE Vol. 6437 643702, separates the subject and the observer from each other using a blackout curtain.

On the other hand, in order to receive acoustic waves efficiently, it is desirable for the acoustic-wave measuring apparatus to move an acoustic-wave probe, which is an acoustic-wave detecting unit, to a precise predetermined measurement position of the subject and detect the acoustic waves. Furthermore, to generate acoustic waves effectively, it is desirable to move also an irradiation unit that irradiates the subject to the predetermined measurement position and irradiate the subject. For these purposes, the observer must check the measurement position on the subject and move the acoustic-wave probe and the irradiation unit to the desired measurement position. However, since the apparatus described by Manohar, et al., separates the subject and the observer from each other with the blackout curtain, it has a problem in that the observer cannot visually observe the subject and it is difficult to move the irradiation unit to the measurement position with high accuracy. Another measuring method moves the irradiation unit to the measurement position with the blackout curtain opened so as to visually align the irradiation unit with the subject without irradiation of light. In this case, however, the operation of opening and closing the blackout curtain is performed for every measurement, which may often cause the observer to forget to close the blackout curtain or a gap to be generated due to incomplete closing of the blackout curtain.

SUMMARY OF THE INVENTION

One aspect of the present invention relates to an acoustic-wave measuring apparatus that includes a holding unit configured to hold a subject; an irradiation unit configured to irradiate the subject with light; an acoustic-wave detecting unit configured to receive acoustic waves generated in the subject due to irradiation with the light via the holding unit; an image pickup unit configured to acquire an image of the subject; a position designating unit configured to designate a measurement position on the image acquired by the image pickup unit; a coordinate transforming unit configured to transform coordinates of the measurement position on the image to coordinates of a corresponding position on the holding unit; and a position control unit configured to move at least one of the irradiation unit and the acoustic-wave detecting unit to the corresponding position on the holding unit.

Another aspect of the present invention relates to an acoustic-wave measuring method. The method includes irradiating a subject with light using an irradiating unit and receiving acoustic waves that are generated from the subject due to irradiation with the light via the holding unit. More specifically, the method includes an image pickup step of acquiring an image of the subject; a position designation step of designating a measurement position on the image acquired by the image pickup step; a coordinate transforming step of transforming coordinates of the measurement position on the image acquired by the image pickup step to coordinates of a corresponding position on the holding unit; and a position control step of moving at least one of the irradiation unit and the acoustic-wave detecting unit to the corresponding position on the holding unit.

Further features of the present invention will become apparent to persons having ordinary skill in the art from the following description of exemplary embodiments with reference to the attached drawings.

DESCRIPTION OF THE EMBODIMENTS

Figure 1A:
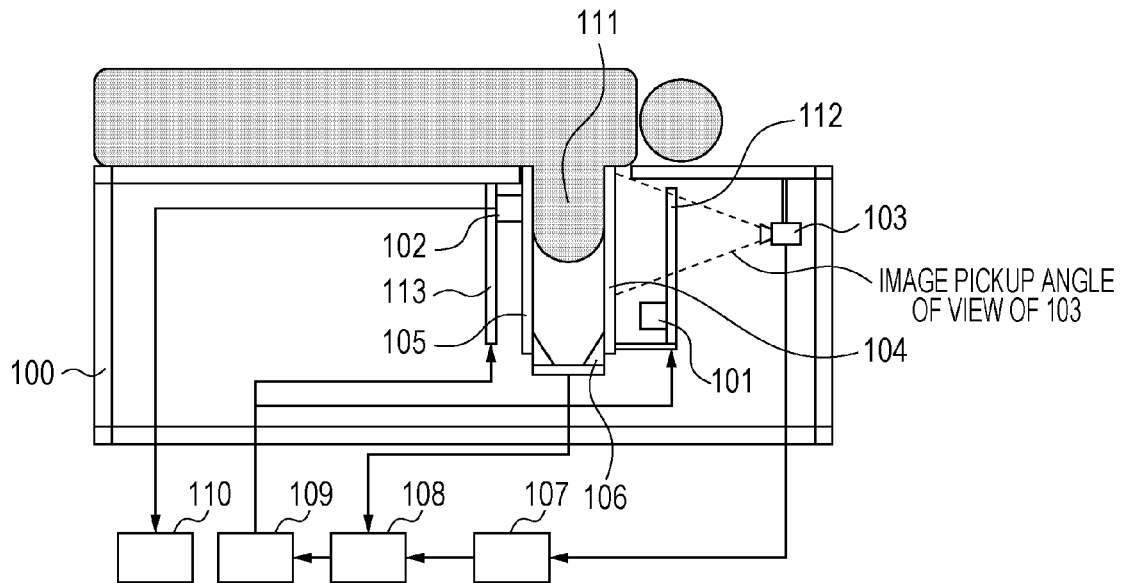
FIG. 1A is a schematic diagram showing in outline an acoustic-wave measuring apparatus according to a first embodiment.
Figure 1B:
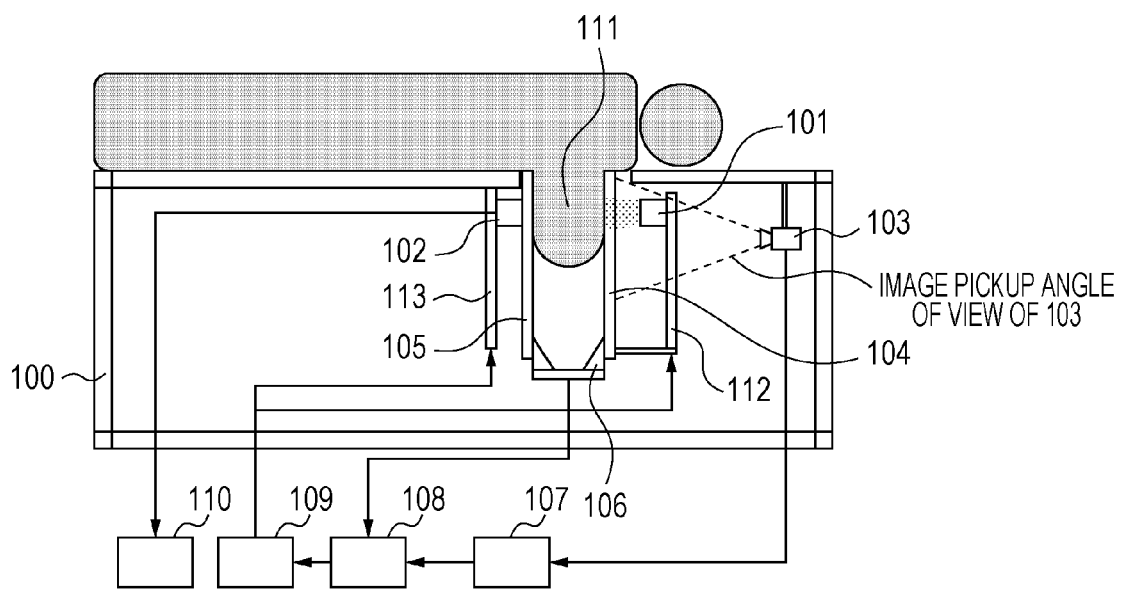
FIG. 1B is a schematic diagram of the acoustic-wave measuring apparatus.

In the present invention, acoustic waves include sound waves, ultrasonic waves, and photoacoustic waves and refers to elastic waves generated when a subject is irradiated with light (electromagnetic waves), such as near infrared light.
First Embodiment An acoustic-wave measuring apparatus according to a first embodiment of the present invention includes a holding apparatus which holds a subject to be examined (e.g., human tissue, such as a breast) and a camera, which is an image pickup unit that acquires an image of the subject. A measurement position is designated on an image acquired by the camera, and at least one of an irradiation unit and an acoustic-wave detecting unit is moved to a corresponding position on the subject.
Apparatus Configuration FIGS. 1A and 1B are side views showing in outline the acoustic-wave measuring apparatus according to the first embodiment of the present invention. FIG. 1A is a schematic diagram showing a state in which an irradiation unit 101 is out of the region imaged by a camera 103 (hereinafter the region imaged by camera 103 is referred to an image pickup region). FIG. 1B is a schematic diagram showing a state in which the irradiation unit 101 is moved to the image pickup region of the camera 103 and irradiates the measurement position with light.

The acoustic-wave measuring apparatus according to the embodiment of the present invention generates light (pulsed light) from a light source (not shown) and irradiates a subject 111 using the irradiation unit 101. This embodiment prevents the light irradiating the subject 111 from leaking to the outside, by using a casing 100, such as a housing or outer covering made of a material that can block the irradiating light. A light absorbing substance (the subject to be examined, such as a tumor) in the subject 111 absorbs light energy and generates acoustic waves. The generated acoustic waves propagate in the subject 111 and traverse a fixed holding plate 105 to reach an acoustic-wave probe 102. The acoustic-wave probe 102 may also be referred to as an acoustic-wave detecting unit, and the fixed holding plate 105 may be referred to as fixed section of a holding unit. The acoustic-wave probe 102 receives the acoustic waves and converts them to an electrical signal and outputs the electric signal to a photoacoustic-wave processing unit 110, which is also referred to as a signal processing unit. The photoacoustic-wave processing unit 110 generates photoacoustic image data (reconfigures an image) using the input signal. The camera 103, which is an example of an image pickup unit, acquires an image of the subject 111 via a movable holding plate 104 to obtain image information. The movable holding plate 104 may be referred to as a movable section of the holding unit. A measurement-position designating unit 107 enables an observer to designate a measurement position on the basis of the image information obtained by the camera 103. The measurement position designated by the observer is output, as pixel coordinates, to a coordinate transforming unit 108. The coordinate transforming unit 108 may be implemented as a self-contained central processing unit (CPU) or a computer-implemented program. The coordinate transforming unit 108 transforms the pixel coordinates received from the measurement-position designating unit 107 to coordinates on the movable holding plate 104 (on-holding-plate coordinates). At that time, the coordinate transformation is performed using the distance between the fixed holding plate 105 and the movable holding plate 104, which is measured by a distance measuring unit 106. The transformed coordinates are output to a position control unit 109. The position control unit 109 may be either a computer-implemented program or hardware electronic circuit that can generate control signals based on the transformed coordinates. Specifically, the position control unit 109 controls at least one of a probe driving mechanism 113 and an irradiation-unit driving mechanism 112, which are moving units, to respectively move at least one of the acoustic-wave probe 102 and the irradiation unit 101.

The light source, not illustrated in the present invention, may include at least one coherent or incoherent pulsed light source capable of producing pulsed light of wavelengths in the biological window. To produce a photoacoustic effect, pulsed light with a pulse width (FWHM) of several hundred nanoseconds or less and more preferably from 5 nanoseconds to 50 nanoseconds is preferable. In the case of measurement of suspect tumorous tissue, such as breast cancer or the like, the light source preferably generates light with a specified wavelength that is absorbed by a specified component (for example, hemoglobin) of components constituting a living organism. A preferably light source may be a laser that produces short pulses of light with a large output; but instead of the laser, a light-emitting diode may also be used. Examples of the laser include a solid-state laser, a gas laser, a dye laser, and a semiconductor laser, each of which may be a modulated continuous wave (CW) laser or a pulsed (e.g., mode locked) laser.

The irradiation unit 101 irradiates the subject 111 by a method suitable for measuring the light from the light source. Although in this embodiment the irradiation unit 101 irradiates the subject 111 from the side opposite to the acoustic-wave probe 102, the present invention is not limited thereto. For example, the subject 111 may be irradiated either from the same side as the acoustic-wave probe 102 or from both sides of the subject 111. Since the sound pressure of acoustic waves is proportional to the intensity of the light, the subject 111 may be irradiated not only from one side of the subject 111 but also from a plurality of sides of the subject 111, so that the signal-to-noise ratio (S/N) of the signal can be increased. Concrete examples of the irradiation unit 101 include optical components, such as a mirror or a lens that collects, magnifies, or changes the shape of light; a prism that disperses, refracts, and reflects light, one or more optical fibers, or a combination of the foregoing that can efficiently deliver light from the light source to the subject 111. Such optical components may be any components provided that they can irradiate the subject 111 with the light emitted from the light source by a desired method (irradiating direction, shape, and so on) in addition to the above. Furthermore, the irradiation region on the subject 111 may be movable on the subject 111, so that a wider irradiation region can be obtained. In addition, as illustrated in FIGS. 1A and 1B, the irradiation unit 101 itself can be moved relative to the subject 111. Furthermore, the region of the subject 111 irradiated with light may be moved in synchronization with the acoustic-wave probe 102. In the case where the light source is small, the light source itself may be used as the irradiation unit 101, and the light source itself may be mechanically moved.

The acoustic-wave probe 102, which is an acoustic-wave detecting unit, converts acoustic waves into an electrical signal. The acoustic-wave probe 102 may be any conversion element that can detect acoustic waves and convert the acoustic waves to an electrical signal. To that end, for example, a conversion element that uses a piezoelectric phenomenon, a conversion element that uses resonance of light, and a conversion element that uses changes in capacitance may be used. Furthermore, an element array composed of a plurality of conversion elements may be used, so that acoustic waves can be received across a wide region. The acoustic waves are received by the acoustic-wave probe 102, and the electric signal proportional to the acoustic waves is input to the photoacoustic-wave processing unit 110. Although the acoustic-wave probe 102 in FIGS. 1A and 1B is provided on the fixed holding plate 105, acoustic-wave probe 102 may be provided on the movable holding plate 104 as well.

The photoacoustic-wave processing unit 110, which may be a signal processing section, may be either a computer-implemented program or an electronic circuit that can digitize the electric signal and generate image data corresponding to the acoustic waves received by the photoacoustic-wave probe 102. The photoacoustic-wave processing unit 110 generates acoustic image data (reconfigures an image) using back projection in a time domain or a Fourier domain, which is normally used in tomography technology. The acoustic image data in the present invention is data indicating information on the interior of the subject 111, irrespective of two-dimensional or three-dimensional data, (biological information, such as an initial sound pressure distribution and a light absorption coefficient distribution of the interior of the living organism). Two-dimensional photoacoustic image data is composed of a plurality of items of pixel data, and three-dimensional photoacoustic image data is composed of a plurality of items of voxel data.

The fixed holding plate 105 and the movable holding plate 104 are holding units for holding the subject 111 and keeping the shape of at least part of the subject 111 constant. As shown in FIGS. 1A and 1B, holding the subject 111 from opposing sides allows the subject 111 to be fixed in position during measurement. Advantageously, keeping the subject 111 fixed during measurement can reduce a position error due to a body motion and so on. Pressing the subject 111 allows light to efficiently reach the depths of the subject 111. A holding unit on which the irradiation unit 101 is provided (the movable holding plate 104 in FIGS. 1A and 1B) may be a member having high light transmittance. A holding unit on which the acoustic-wave probe 102 is provided (the fixed holding plate 105 in FIGS. 1A and 1B) may be a member having a property of acoustic matching with the subject 111 and the acoustic-wave probe 102 (having similar acoustic impedance). To enhance the acoustic matching property, an acoustic matching material, such as gel, may be interposed between the holding units and the subject 111 and between the holding units and the acoustic-wave probe 102. The holding units are not restricted to having the above-described configuration. For example, instead of having a fixed section and a movable section, both holding plates may be movable. In addition, instead of the configuration in which the subject 111 is held by holding plates from both sides, a configuration in which the subject 111 is held from below with a bowl-shaped member may be provided.

The casing 100 has the function of preventing the light irradiating the subject 111 from leaking to the outside by enclosing the peripheries of the irradiation unit 101, the acoustic-wave probe 102, and so on. This prevents the observer from being irradiated with light. The casing 100 of this embodiment also has the function of protecting the person being examined from irradiated light.

The camera 103, which is an image pickup unit, is disposed in the casing 100 and acquires image information on the subject 111. Examples of the camera 103 include a charge coupled device (CCD) sensor-based camera and a complementary metal oxide semiconductor (CMOS) sensor-based camera. The camera 103 of this embodiment is fixed to the casing 100. When the camera 103 is to acquire an image of the subject 111, the irradiation unit 101 may be moved out of the image pickup region so as not to overlap with the subject 111. Although the camera 103 in FIGS. 1A and 1B is shown near the movable holding plate 104, the camera 103 may be provided near the fixed holding plate 105.

The irradiation-unit driving mechanism 112, which is a moving unit, can move the irradiation unit 101 to any position in or out of the image pickup region of the camera 103.

Figure 2A:
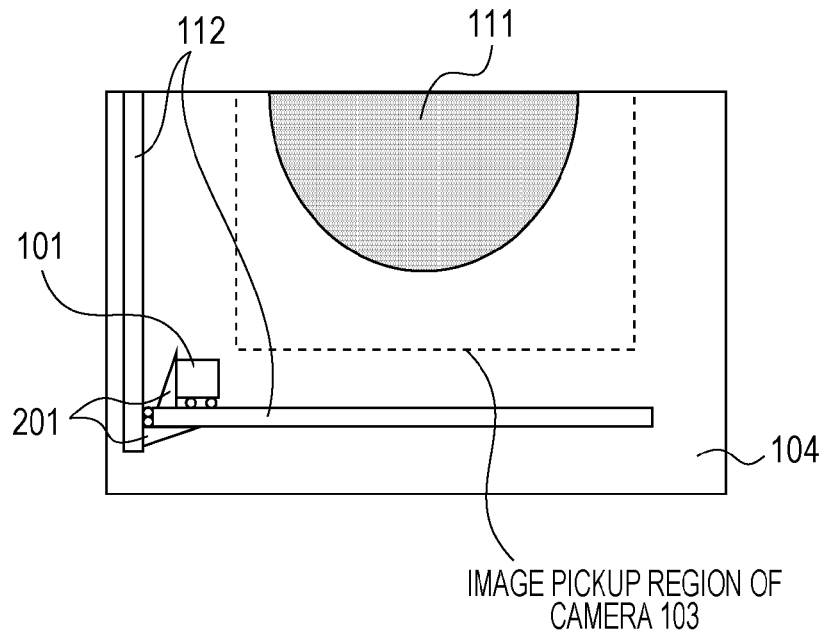
FIG. 2A is a schematic diagram of the apparatus as viewed from a camera.
Figure 2B:
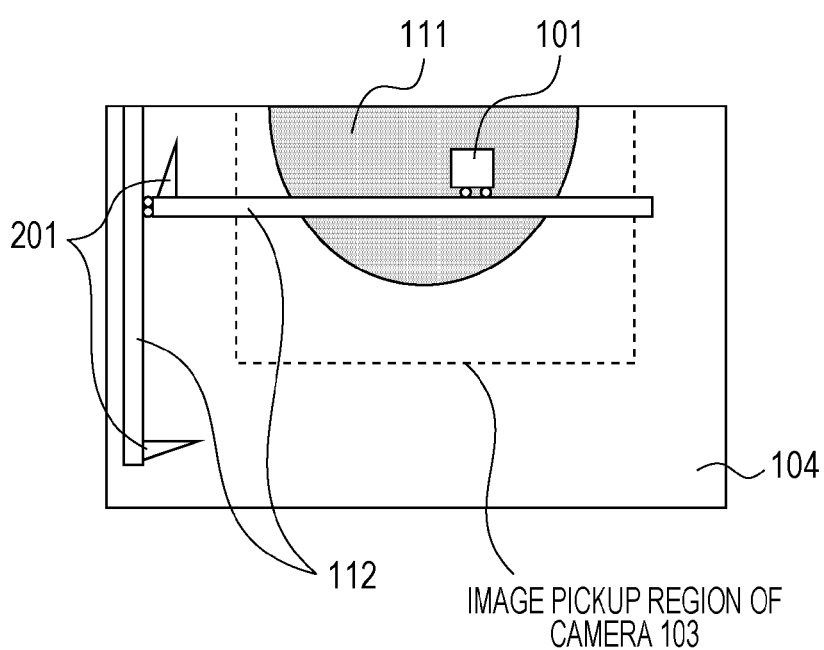
FIG. 2B is a schematic diagram of the apparatus as viewed from the camera.

FIGS. 2A and 2B are schematic diagrams of the apparatus as viewed from the camera 103 side. FIG. 2A is a schematic diagram showing a state in which the irradiation unit 101 is moved out of the image pickup region of the camera 103. FIG. 2B is a schematic diagram showing a state in which the irradiation unit 101 is moved into the image pickup region of the camera 103. The irradiation-unit driving mechanism 112 has a mechanism for driving the irradiation unit 101 independently in the horizontal direction and the vertical direction. Examples of the driving mechanism include a motor and a rack-and-pinion, a motor and a belt, and a linear motor. The irradiation-unit driving mechanism 112 has an origin sensor 201. The position of the origin sensor 201 is designed so that the position of the irradiation unit 101 defined by the origin sensor 201 is out of the image pickup region of the camera 103. Examples of the origin sensor 201 include a contact sensor, an optical sensor, and an origin marker of an absolute encoder. The irradiation-unit driving mechanism 112 is controlled by the position control unit 109. To move the irradiation unit 101 out of the image pickup region of the camera 103, an instruction to move the irradiation unit 101 to the original position is sent from the position control unit 109 to the irradiation-unit driving mechanism 112. Thus, the state in FIG. 1A is achieved by moving the irradiation unit 101 out of the image pickup region of the camera 103, as shown in FIG. 2A. To move the irradiation unit 101 into the image pickup region of the camera 103, an instruction to move the irradiation unit 101 to a position in the image pickup region is sent from the position control unit 109 to the irradiation-unit driving mechanism 112. Thus, the state in FIG. 1B is achieved by moving the irradiation unit 101 into the image pickup region of the camera 103, as shown in FIG. 2B.

The probe driving mechanism 113, which is a moving unit, should move the acoustic-wave probe 102 to a position opposing the irradiation unit 101, with the subject 111 therebetween. The probe driving mechanism 113 is controlled by the position control unit 109. In the case where the camera 103 is disposed near the acoustic-wave probe 102, the irradiation unit 101 should be moved as described above so as to prevent the subject 111 from overlapping with the acoustic-wave probe 102 during image acquisition.

The distance measuring unit 106 measures the distance between the fixed holding plate 105 and the movable holding plate 104. The distance here is a distance in the optical axis of the camera 103. One end of the distance measuring unit 106 is fixed to the fixed holding plate 105, and the other end is fixed to the movable holding plate 104. Distances that differ depending on the characteristics (sizes and so on) of the individual subjects 111 are output to the coordinate transforming unit 108.

The measurement-position designating unit 107 is for the observer to designate a measurement position on an image acquired by the camera 103, such as mouse, keyboard or touch panel. An image is displayed on a display, such as a monitor, using image information from the camera 103. An observer designates a measurement position on the displayed image with a mouse or designates a measurement position on a screen having a contact position detection sensor with a finger. The measurement position may be designated by inputting the coordinates of a measurement position on the image using a keyboard or the like. The designated measurement position is output as pixel coordinates on the image to the coordinate transforming unit 108.

The coordinate transforming unit 108 transforms the pixel coordinates output from the measurement-position designating unit 107 to the coordinates of a position corresponding to the pixel coordinates on the movable holding unit (on the movable holding plate 104 in this embodiment). At that time, the transformation is made using the distance between the fixed holding plate 105 and the movable holding plate 104 measured by the distance measuring unit 106. The transformed coordinates are output to the position control unit 109.

The position control unit 109 controls the probe driving mechanism 113 and the irradiation-unit driving mechanism 112 to move at least one of the acoustic-wave probe 102 and the irradiation unit 101. For example, the irradiation unit 101 can be moved to the coordinate position output from the coordinate transforming unit 108 or to an original position defined by the origin sensor 201.

Measurement Flow

Figure 3:
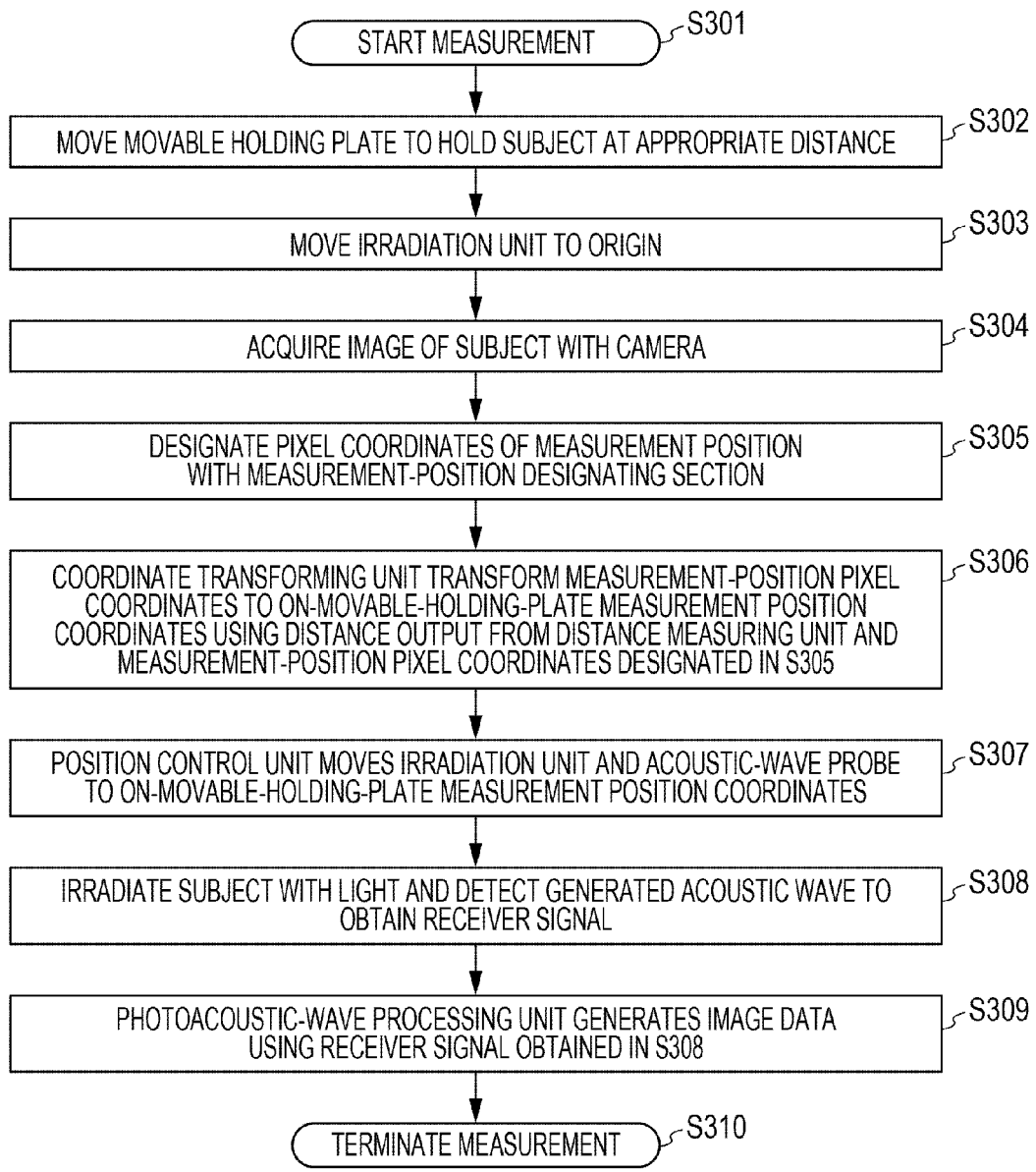
FIG. 3 is a flowchart of an exemplary process for measurement in the first embodiment.

The measurement flow of this embodiment is shown in FIG. 3. The individual steps of the measurement flow will be described in detail with reference to FIGS. 1A and 1B and FIG. 3. The following description is made using a configuration example in which the holding units composed of the fixed holding unit and the movable holding unit is provided, and the acoustic-wave probe 102 is provided on the fixed holding unit side, and the irradiation unit 101 is provided nearer to the movable holding unit, as in FIGS. 1A and 1B. However, the present invention is not limited to such a configuration, as described above.

First, the measurement process is started at step 301 (abbreviated in the drawing as S301), the subject 111 is positioned between the fixed holding plate 105 and the movable holding plate 104, and the observer moves the movable holding plate 104 to hold the subject 111 in the desired position at step 302. At that time, the subject 111 may be pressed to be held as thin as possible, so as to optimize the S/N ratio of a received signal obtained and the depth of measurement. After completion of the holding, that is—once the subject 111 is positioned and held in the desired position—the distance between the fixed holding plate 105 and the movable holding plate 104 is measured by the distance measuring unit 106.

In step 303, the irradiation unit 101 is moved to the original position. The irradiation-unit driving mechanism 112 is driven by the position control unit 109, and the irradiation unit 101 is moved to the original position designated by the origin sensor 201.

In step 304 (image pickup step), an image of the subject 111 is acquired by the camera 103. Since the irradiation unit 101 has been moved to the original position outside the image pickup region of the camera 103 in step 303, an image of the entire subject 111 including the measurement position can be acquired.

In step 305, the observer designates the measurement position on the image using pixel coordinates on the basis of the image information on the subject 111 obtained in step 304, and thus, the pixel coordinates of the measurement position (measurement-position pixel coordinates) can be obtained.

Figure 4:
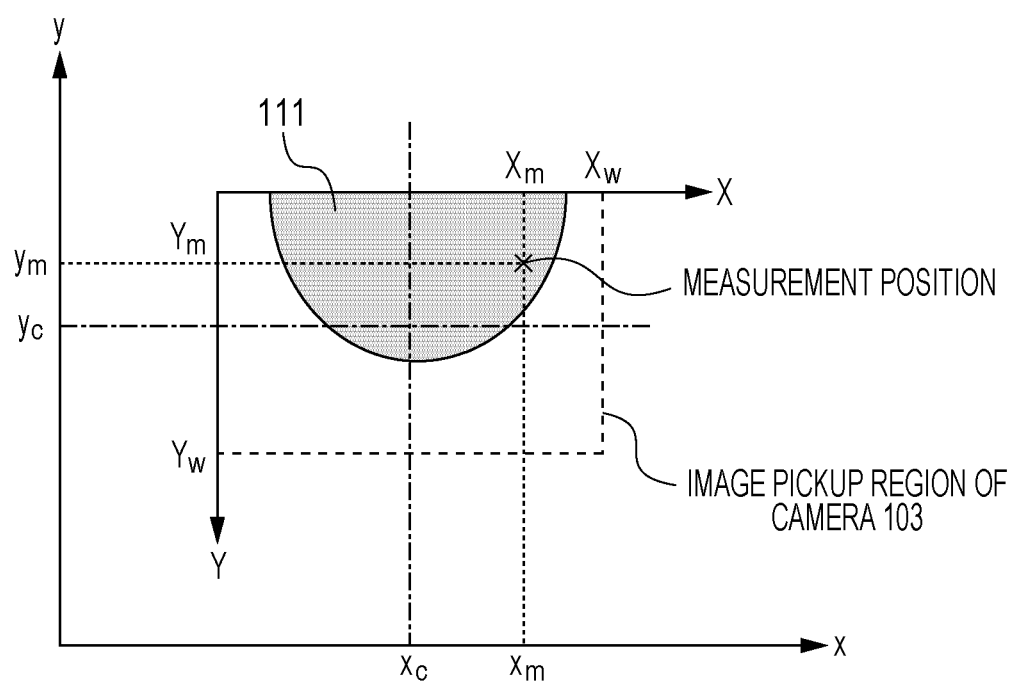
FIG. 4 is a graph showing the relationship between the pixel coordinates of a measurement position and coordinates on a movable holding plate.
Figure 5:
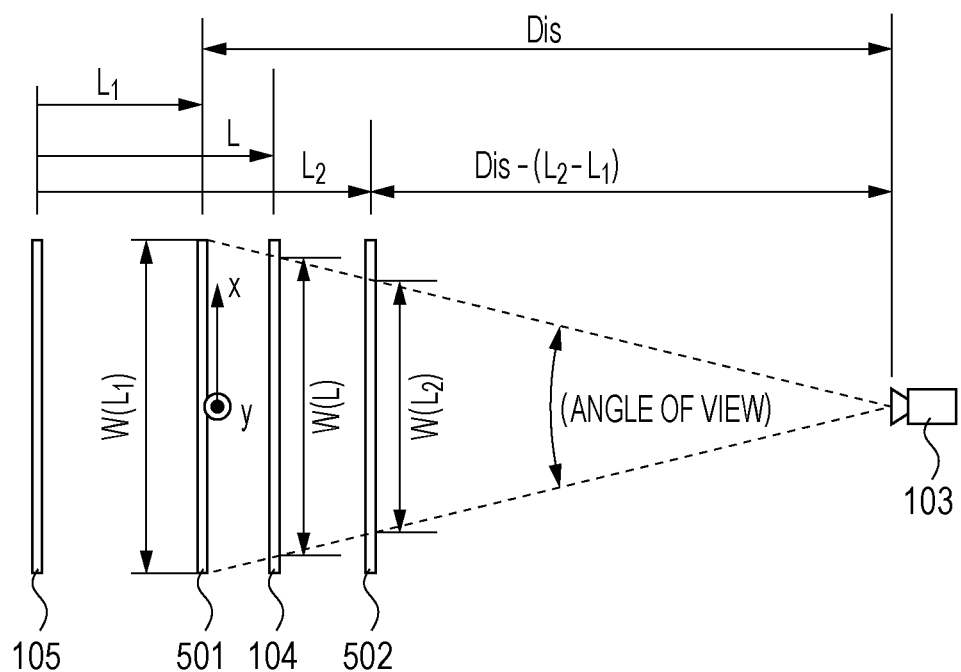
FIG. 5 is a schematic diagram of a fixed holding plate, the movable holding plate, and the camera, as viewed from the top of the apparatus.

A process in step 306 (coordinate transforming step) will be described with reference to FIGS. 4 and 5. FIG. 4 is a graph showing pixel coordinates on the image and coordinates on the movable holding plate 104. The coordinate transforming unit 108 transforms the pixel coordinates ($X_m$, $Y_m$) of the measurement position designated by the observer in step 305 to measurement position coordinates ($x_m$, $y_m$) on the movable holding plate 104 (on-movable-holding-plate measurement position coordinates). The on-movable-holding-plate measurement position coordinates are expressed, for example, by values in millimeters or micrometers.

Next, transformation equations will be described. FIG. 5 is a schematic diagram of the fixed holding plate 105, the movable holding plate 104, and the camera 103, as viewed from the top of the apparatus. The movable holding plate 104 can take any distance L. Reference numerals 501 and 502 denote the positions of the movable holding plate 104 when $L=L_1$ and $L=L_2$, respectively. The image pickup width of the camera 103 at distance L is denoted by W(L). As shown in FIG. 5, the image pickup width W changes depending on the position of the movable holding plate 104. The distance between the movable holding plate 104 and the camera 103 when $L=L_1$ is denoted by Dis. Dis can be expressed as the following Exp. (1) from the relation of an isosceles triangle with the vertex at the angle of view in FIG. 5.

$$Dis = (L_2 - L_1)\left(1 - \frac{W(L_2)}{W(L_1)}\right)^{-1} \quad \text{Exp. (1)}$$

From the coordinate relationship shown in FIG. 4, transformation equation for transforming measurement-position pixel coordinates to on-movable-holding-plate measurement position coordinates can be expressed using Dis in Exp. (1), $$x_m = x_c + \left(X_m - \frac{X_w}{2}\right) \times \frac{W(L_1) \times \left(\frac{Dis - (L - L_1)}{Dis}\right)}{X_w} \quad \text{Exp. (2)}$$

$$y_m = y_c - \left(Y_m - \frac{Y_w}{2}\right) \times \frac{W(L_1) \times \left(\frac{Dis - (L - L_1)}{Dis}\right)}{X_w}$$

Transformation of pixel coordinate $X_m$ to position coordinate $x_m$ by Exp. (2) will be described below. Referring to FIG. 4, reference sign X denotes a horizontal pixel coordinate axis, Y denotes a vertical pixel coordinate axis, $X_m$ denotes a measurement-position horizontal pixel coordinate, $Y_m$ denotes a measurement-position vertical pixel coordinate, $X_w$ denotes an image-pickup-region-end horizontal pixel coordinate, and $Y_w$ denotes an image-pickup-region-end vertical pixel coordinate. Reference sign x denotes an on-movable-holding-plate horizontal coordinate axis, y denotes an on-movable-holding-plate vertical coordinate axis, $x_m$ denotes a measurement-position horizontal coordinate, $y_m$ denotes a measurement-position vertical coordinate, $x_c$ denotes a horizontal coordinate at the center of image pickup region, and $y_c$ denotes a vertical coordinate at the center of image pickup region.

$$W(L_1) \times \left(\frac{Dis - (L - L_1)}{Dis}\right) \quad \text{Exp. (3)}$$

Exp. (3) in Exp. (2) is a transformation coefficient determined from the distance between the camera 103 and a measurement position. Exp. (3) expresses an image pickup width W(L) at any distance L. By dividing the image pickup width W(L) expressed as Exp. (3) by the image-pickup-region-end horizontal pixel coordinate $X_w$ in FIG. 4, the distance of an on-movable-holding-plate coordinates per pixel (Exp. (4)) can be given.

$$\frac{W(L_1) \times \left(\frac{Dis - (L - L_1)}{Dis}\right)}{X_w} \quad \text{Exp. (4)}$$

By multiplying Exp. (5), which is the amount of pixels from the center of the image to the measurement-position horizontal pixel coordinate $X_m$ in Exp. (2), by Exp. (4), $$\left(X_m - \frac{X_w}{2}\right) \quad \text{Exp. (5)}$$

the distance of an on-movable-holding-plate coordinates, expressed as Exp. (6) can be obtained.

$$x_m - x_c = \left(X_m - \frac{X_w}{2}\right) \times \frac{W(L_1) \times \left(\frac{Dis - (L - L_1)}{Dis}\right)}{X_w} \quad \text{Exp. (6)}$$

By transposing $x_c$ in Exp. (6) to the left term, $x_m$ in Exp. (2) can be found. Although the above is for the horizontal direction, the same applies to the vertical direction, that is, transformation from $Y_m$ to $y_m$.

$L_1$, $L_2$, $W(L_1)$, and $W(L_2)$ are known values measured in advance, and $x_c$, $x_c$, $X_w$, and $Y_w$ are given in advance as specification values of the apparatus. By substituting the distance between the fixed holding plate 105 and the movable holding plate 104 measured in step 302 for L in Exp. (2), and substituting the measurement-position pixel coordinates obtained in step 305 for $(X_m, Y_m)$ in Exp. (2), the on-movable-holding-plate measurement position coordinates $(x_m, y_m)$ can be given. Even if the distance between the movable holding plate 104 and the camera 103 changes, the relationship between the pixel coordinates $(X_m, Y_m)$ and the on-movable-holding-plate measurement position coordinates $(x_m, y_m)$ can be corrected properly by performing step 306.

Referring back to FIG. 3, in step 307 (position control step), the irradiation unit 101 is moved by the position control unit 109 to the on-movable-holding-plate measurement position coordinates $(x_m, y_m)$ obtained in step 306. Since transformation with consideration of the distance between the fixed holding plate 105 and the movable holding plate 104 is performed in step 306, the irradiation unit 101 can be moved with high accuracy. In this step, not only the irradiation unit 101 but also the acoustic-wave probe 102 should be moved to the coordinates $(x_m, y_m)$ of the measurement position on the fixed holding plate 105. Here, the measurement position is a position on the subject 111 to be measured in more detail or a start position in the case where measurement is performed while the acoustic-wave probe 102 and the irradiation unit 101 are being moved.

In step 308, the irradiation unit 101 irradiates the subject 111 with light, and the acoustic-wave probe 102 detects generated acoustic waves to obtain a receiver signal. In step 309, the photoacoustic-wave processing unit 110 generates photoacoustic image data using the receiver signal obtained in step 308. The photoacoustic image data is presented to the observer as, for example, numerical information or an image, on a display unit (not shown), and the measurement ends at step 310.

Providing an image pickup unit, such as the camera 103, allows designation of a measurement position even in an acoustic-wave measuring apparatus in which visual designation of a measurement position is difficult. Furthermore, providing the irradiation-unit driving mechanism 112 that moves the irradiation unit 101 out of the image pickup region of the camera 103 and the distance measuring unit 106 allows high-accuracy designation of a measurement position.

Second Embodiment

In a second embodiment, a case in which the distance between the image pickup unit that acquires an image of the subject and the movable holding unit is held constant will be particularly described. The other configurations are the same as those of the first embodiment.

Apparatus Configuration

Figure 6:
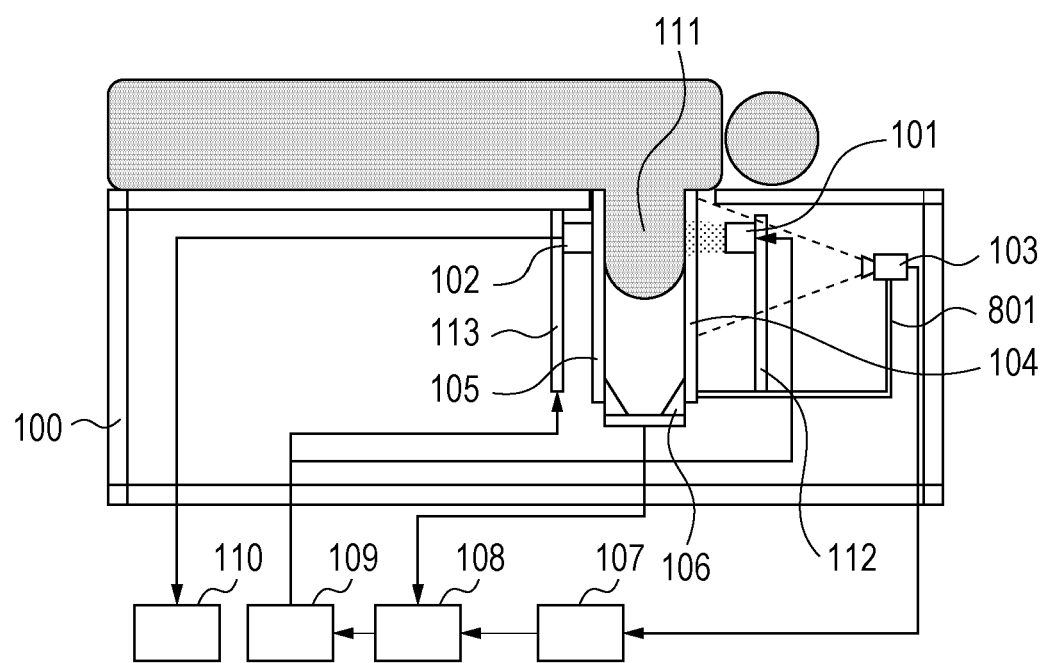
FIG. 6 is a schematic diagram showing in outline an acoustic-wave measuring apparatus according to a second embodiment.

FIG. 6 is a schematic diagram showing the configuration of an acoustic-wave measuring apparatus according to a second embodiment of the present invention. In this embodiment, although the details of processing in the coordinate transforming unit differ from those of the first embodiment, the other components are the same as those of the first embodiment; therefore, descriptions of the same terms are omitted.

A fixing member 801, which is a distance fixing unit, fixes the movable holding plate 104 and the camera 103 a predetermined distance. The fixing member 801 is designed to fix the distance between the movable holding plate 104 and the camera 103 to a certain value. Therefore, even if the movable holding plate 104 moves, the distance between the movable holding plate 104 and the camera 103 is kept constant. The fixing member 801 may be disposed out of the image pickup region of the camera 103. The coordinate transforming unit 108 transforms pixel coordinates output from the measurement-position designating unit 107 to coordinates on the movable holding plate 104. At that time, the transformation is performed using the distance determined depending on the fixing member 801. The transformed coordinates are output to the position control unit 109.

Measurement Flow

Figure 7:
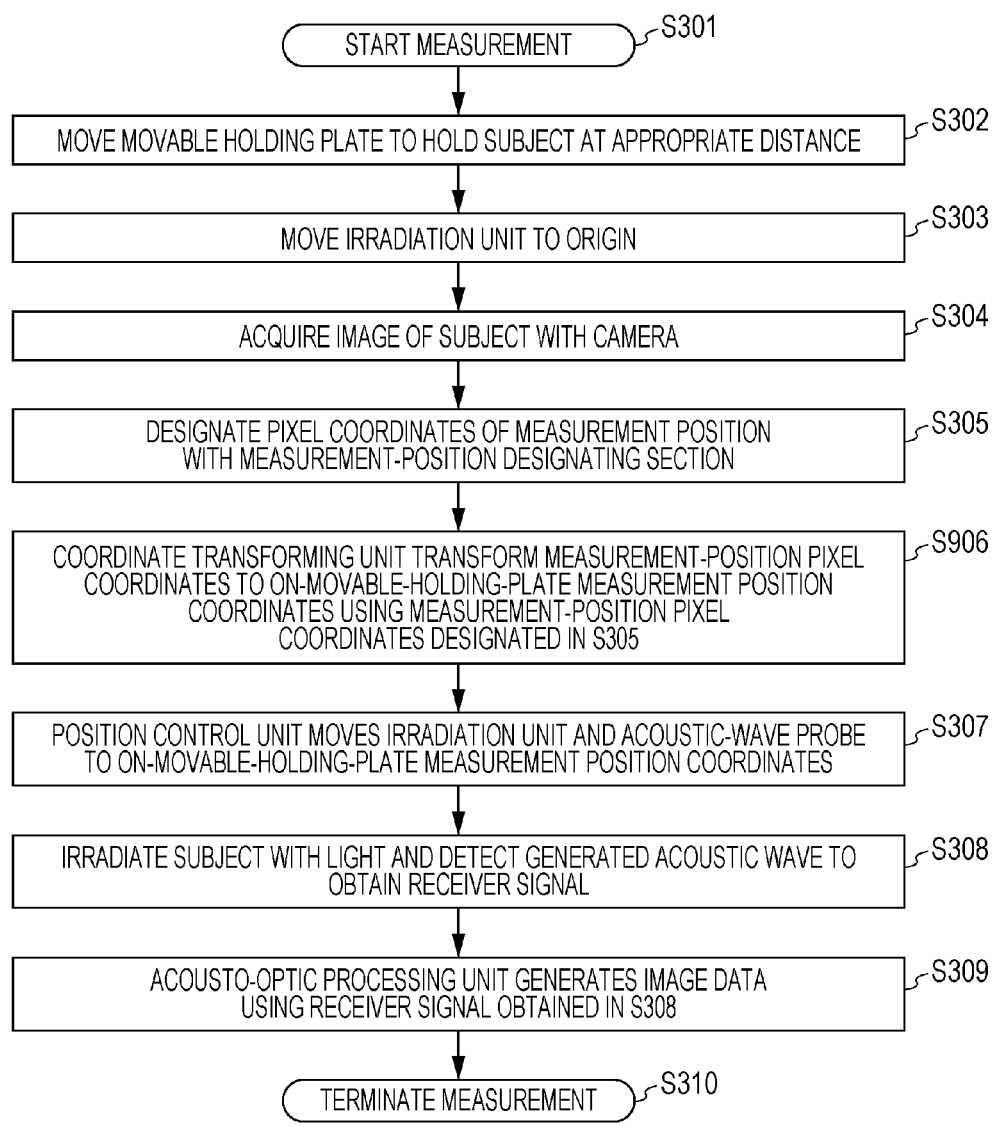
FIG. 7 is a flowchart of an exemplary process for measurement in the second embodiment.

The measurement flow of the second embodiment is shown in FIG. 7. Although the coordinate transforming step (step 906) of this embodiment differs from step 306 of the first embodiment, the other steps are the same as in FIG. 3; therefore, descriptions thereof will be omitted.

Figure 8:
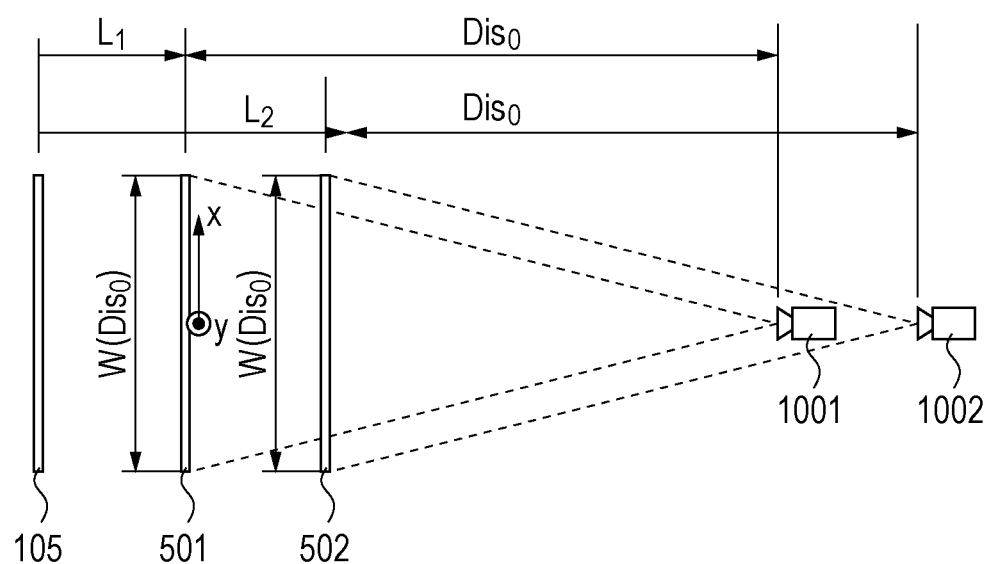
FIG. 8 is a schematic diagram of the fixed holding plate, the movable holding plate, and the camera, as viewed from the top of the apparatus.

A process in step 906 will be described with reference to FIG. 8. FIG. 8 is a schematic diagram of the fixed holding plate 105, the movable holding plate 104, and the camera 103, as viewed from the top of the apparatus. Reference numerals 1001 and 1002 denote the positions of the camera 103 when the distance between the fixed holding plate 105 and the movable holding plate 104 is $L_1$ and $L_2$, respectively. Since the distance $Dis_0$ between the movable holding plate 104 and the camera 103 is constant by means of the fixing member 801, the image pickup width W of the camera 103 depends on $Dis_0$ at either of the distances $L_1$ and $L_2$. Referring to FIGS. 4 and 8, transformation equations for transforming measurement-position pixel coordinates to on-movable-holding-plate measurement position coordinates can be expressed as Exp. (7).

$$x_m = x_c + \left(\frac{X_m - \frac{X_w}{2}}{X_w}\right) \times W(Dis_0) \qquad \text{Exp. (7)}$$

$$y_m = y_c - \left(\frac{Y_m - \frac{Y_w}{2}}{X_w}\right) \times W(Dis_0)$$

W(Dis$_0$) in Exp. (7) is a transformation coefficient determined from the distance between the image pickup unit and a measurement position. Since Dis$_0$ is a specification value of the apparatus, determined depending on the fixing member 801, the transformation coefficient W(Dis$_0$) is given in advance. By substituting the measurement-position pixel coordinates obtained in step 305 for (X$_m$, Y$_m$) in Exp. (2), the on-movable-holding-plate measurement position coordinates (x$_m$, y$_m$) can be obtained.

Thus, providing the camera 103 allows designation of a measurement position even in an acoustic-wave measuring apparatus in which visual designation of a measurement position is difficult. Furthermore, providing the fixing member 801 prevents the distance between the movable holding plate 104 and the camera 103 from changing even if the subject holding thickness changes, thereby facilitating the process of the coordinate transforming step.

In accordance with at least one embodiment of the present invention, an acoustic-wave measuring apparatus enables, among other things, designation of a measurement position with high accuracy and accurate detection of acoustic waves at a desired position. While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Patent Application No. 2010-101300 filed on Apr. 26, 2010, which is hereby incorporated by reference herein in its entirety.

What is claimed is:

1. An acoustic-wave measuring apparatus comprising:
   a holding unit configured to hold a subject;
   an irradiation unit configured to irradiate the subject with light;
   an acoustic-wave detecting unit configured to receive acoustic waves generated within the subject due to irradiation with the light irradiated from the irradiation unit, the acoustic-wave detecting unit being disposed at a side of the holding unit opposite to the subject;
   an image pickup unit configured to acquire, through the holding unit, an image of a shape of the subject held by the holding unit;
   a coordinate transforming unit configured to transform coordinates of a measurement position designated by an observer, on the image acquired by the image pickup unit to coordinates on the holding unit; and
   a position control unit configured to move at least one of the irradiation unit and the acoustic-wave detecting unit on the holding unit based on information output from the coordinate transforming unit.

2. The acoustic-wave measuring apparatus according to claim 1, wherein the coordinate transforming unit transforms the coordinates of the measurement position on the image to the coordinates on the holding unit using a transformation coefficient determined from the distance between the holding unit and the image pickup unit.

3. The acoustic-wave measuring apparatus according to claim 2, wherein:
   the holding unit includes a fixed holding section and a movable holding section configured to hold the subject from opposite sides;
   the coordinate transforming unit transforms the coordinates of the measurement position on the image to the coordinates on the movable holding section using a transformation coefficient determined from a distance between the movable holding section and the image pickup unit.

4. The acoustic-wave measuring apparatus according to claim 3, further comprising a distance fixing unit configured to keep the distance between the movable holding section and the image pickup unit constant.

5. An acoustic-wave measuring method, comprising:
   holding a subject with a holding unit;
   irradiating the subject with light irradiated from an irradiation unit;
   an acoustic-wave detecting step of receiving acoustic waves generated within the subject due to irradiation with the light irradiated from the irradiation unit, the acoustic waves being received by an acoustic-wave detecting unit disposed at a side of the holding unit opposite to the subject;
   an image pickup step of acquiring, with an image pickup unit and through the holding unit, an image of a shape of the subject held by the holding unit;
   a coordinate transforming step of transforming coordinates of a measurement position, designated by an observer, on the image acquired in the image pickup step to coordinates on the holding unit; and
   a position control step of moving at least one of the irradiation unit and the acoustic-wave detecting unit on the holding unit based on information obtained at the coordinate transforming step.

6. The acoustic-wave measuring method according to claim 5, wherein in the coordinate transforming step, the coordinates of the measurement position on the image are transformed to the coordinates on the holding unit using a transformation coefficient determined from a distance between the holding unit and the image pickup unit.

7. The acoustic-wave measuring method according to claim 6, wherein:
   in the holding step, the holding unit includes a fixed holding section and a movable holding section configured to hold the subject from opposite sides thereof; and
   in the coordinate transforming step, the coordinates of the measurement position on the image are transformed to the coordinates on the movable holding section using a transformation coefficient determined from a distance between the movable holding section and the image pickup unit.

8. The acoustic-wave measuring method according to claim 7, further comprising a distance measuring step of measuring the distance between the movable holding section and the image pickup unit.

9. An acoustic-wave measuring method, comprising:
   holding a subject with a holding unit;
   irradiating the subject with light irradiated from an irradiation unit;
   an acoustic-wave detecting step of receiving acoustic waves generated within the subject due to irradiation with the light irradiated from the radiation unit, the acoustic waves being received by an acoustic wave detecting unit disposed at a side of the holding unit opposite to the subject;

an image pickup step of acquiring with an image pickup unit an image of a shape of the subject held by the holding unit;

a position designation step of designating a measurement position on the image acquired in the image pickup step;

a coordinate transforming step of transforming coordinates of the measurement position on the image acquired in the image pickup step to coordinates on the holding unit; and a position control step of moving at least one of the irradiation unit and the acoustic-wave detecting unit on the holding unit based on information obtained at the coordinate transforming step.

10. The acoustic-wave measuring apparatus according to claim 1, wherein the image pickup unit is a charge coupled device sensor-based camera or a complementary metal oxide semiconductor sensor-based camera.

11. The acoustic-wave measuring apparatus according to claim 1, wherein at least one of the irradiation unit and the acoustic-wave detecting unit is positioned outside the image pickup region of the image pickup unit when the image pickup unit captures the image of the shape of the subject.

12. The acoustic-wave measuring apparatus according to claim 1, further comprising a position designating unit configured to designate a measurement position on the image acquired by the image pickup unit.

13. The acoustic-wave measuring apparatus according to claim 1, further comprising a casing configured to surround the irradiation unit, the acoustic-wave detecting unit and the holding unit so as to prevent the light irradiated to the subject from being leaked to outside.

14. The acoustic-wave measuring method according to claim 5, wherein, in the image pickup step, the image of the shape of the subject is captured with a charge coupled device sensor-based camera or a complementary metal oxide semiconductor sensor-based camera.

15. The acoustic-wave measuring method according to claim 5, wherein, in the image pickup step, at least one of the irradiation unit and the acoustic-wave detecting unit is positioned outside the image pickup region of the image pickup unit.

16. The acoustic-wave measuring method according to claim 9, wherein, in the image pickup step, the image of the shape of the subject is captured with a charge coupled device sensor-based camera or a complementary metal oxide semiconductor sensor-based camera.

17. The acoustic-wave measuring method according to claim 9, wherein, in the image pickup step, at least one of the irradiation unit and the acoustic-wave detecting unit is positioned outside the image pickup region of the image pickup unit.

18. An acoustic-wave measuring apparatus comprising:
a holding unit configured to hold a subject;
an irradiation unit configured to irradiate the subject with light;
an acoustic-wave detecting unit configured to receive acoustic waves generated within the subject due to the light irradiated to the subject from the irradiation unit, the acoustic-wave detecting unit being disposed at a side of the holding unit opposite to the subject;
an image pickup unit configured to acquire, via the holding unit, an image of a shape of the subject held by the holding unit;
a coordinate transforming unit configured to transform coordinates of a measurement position designated by an observer on the image acquired by the image pickup unit to coordinates on the holding unit; and
a position control unit configured to move at least one of the irradiation unit and the acoustic-wave detecting unit on the holding unit so that the acoustic-wave detecting unit can receive the acoustic waves at the measurement position.

19. The acoustic-wave measuring apparatus according to claim 18, wherein the coordinate transforming unit transforms the coordinates of the measurement position on the image to the coordinates on the holding unit using a transformation coefficient determined from the distance between the holding unit and the image pickup unit.

20. The acoustic-wave measuring apparatus according to claim 19, wherein:
the holding unit includes a fixed holding section and a movable holding section configured to hold the subject from opposite sides thereof;
the coordinate transforming unit transforms the coordinates of the measurement position on the image to the coordinates on the movable holding section using a transformation coefficient determined from a distance between the movable holding section and the image pickup unit.

21. The acoustic-wave measuring apparatus according to claim 20, further comprising a distance fixing unit configured to keep the distance between the movable holding section and the image pickup unit constant.

22. The acoustic-wave measuring apparatus according to claim 18, wherein the image pickup unit is a charge coupled device sensor-based camera or a complementary metal oxide semiconductor sensor-based camera.

23. The acoustic-wave measuring apparatus according to claim 18, wherein at least one of the irradiation unit and the acoustic-wave detecting unit is positioned outside the image pickup region of the image pickup unit when the image pickup unit captures the image of the shape of the subject.

24. The acoustic-wave measuring apparatus according to claim 18, further comprising a position designating unit configured to designate a measurement position on the image acquired by the image pickup unit.

25. The acoustic-wave measuring apparatus according to claim 18, further comprising a casing configured to surround the irradiation unit, the acoustic-wave detecting unit and the holding unit so as to prevent the light irradiated to the subject from being leaked to outside of the casing.

26. An acoustic-wave measuring method, comprising:
holding an subject with a holding unit;
irradiating the subject with light irradiated from an irradiation unit;
an acoustic-wave detecting step of receiving acoustic waves generated within the subject due to the light irradiated to the subject from the irradiation unit, the acoustic-wave detecting unit being disposed at a side of the holding unit opposite to the subject;
an image pickup step of acquiring with an image pickup unit an image of a shape of the subject held by the holding unit;
a coordinate transforming step of transforming coordinates of a measurement position designated by an observer on the image acquired by the image pickup unit to coordinates on the holding unit; and
a position control step of moving at least one of the irradiation unit and the acoustic-wave detecting unit on the holding unit based on information obtained at the coordinate transforming step.

* * * * *